United States Patent [19]
Toman et al.

[11] Patent Number: 5,512,066
[45] Date of Patent: Apr. 30, 1996

[54] TAGGING MATERIALS FOR GASOLINE

[75] Inventors: Jeffrey J. Toman, Oakland; Wilton R. Biggs, Vacaville, both of Calif.

[73] Assignee: Chevron Chemical Company, San Ramon, Calif.

[21] Appl. No.: 468,495

[22] Filed: Jun. 6, 1995

Related U.S. Application Data

[63] Continuation-in-part of Ser. No. 377,541, Jan. 23, 1995, abandoned.

[51] Int. Cl.$^6$ ...................................................... C10L 1/16
[52] U.S. Cl. ................................ 44/300; 585/10; 585/11; 585/14
[58] Field of Search .............................. 44/300; 585/10, 585/11, 14

[56] References Cited

U.S. PATENT DOCUMENTS

| | | | |
|---|---|---|---|
| 2,058,774 | 10/1936 | Colligan | 44/300 |
| 2,265,196 | 12/1941 | Riley | 44/328 |
| 3,682,187 | 8/1972 | Seymour et al. | 137/13 |
| 3,687,148 | 8/1972 | Kruka et al. | 137/13 |
| 3,861,886 | 1/1975 | Meloy | 585/14 |
| 4,141,692 | 2/1979 | Keller | 44/59 |
| 4,209,302 | 6/1980 | Orelup | 44/59 |
| 4,278,444 | 7/1981 | Beyer et al. | 44/59 |
| 4,735,631 | 4/1988 | Orelup | 44/59 |
| 4,764,474 | 8/1988 | Orelup | 436/111 |
| 4,918,020 | 4/1990 | Nowak | 436/56 |
| 5,234,475 | 8/1993 | Malhotra et al. | 44/282 |
| 5,252,106 | 10/1993 | Hallisy | 44/328 |
| 5,279,967 | 1/1994 | Bode | 44/419 |

FOREIGN PATENT DOCUMENTS

0509818A1  10/1992  European Pat. Off. .......... C10L 1/00

Primary Examiner—Jacqueline V. Howard
Attorney, Agent, or Firm—E. A. Schaal; W. K. Turner

[57] ABSTRACT

Gasolines are identified from one another by adding to at least one of the gasolines at least one tagging material which is unique to that gasoline. Each unique tagging material has a number average molecular weight of at least 15,000 and is present at a level of less than 1.0 ppm of the gasoline. In addition, each unique tagging material must be soluble in the composition to be tagged, must not vaporize or thermally degrade at temperatures below about 120° C., must not contribute to degradation of hydrocarbon filterability: and must not contribute to engine harm. A sample of the gasoline is vaporized to form a liquid residue; and the liquid residue is analyzed for the presence of the tagging material in the residue to thereby identify the particular gasoline.

4 Claims, 2 Drawing Sheets

TAGGING MATERIALS FOR GASOLINE

This application is a continuation-in-part application of U.S. Ser. No. 08/377,541, filed Jan. 23, 1995, entitled "Tagging Materials For Gasoline," now abandoned which is hereby incorporated by reference for all purposes.

The present invention relates to gasolines having high molecular weight tagging materials therein to permit identification of the particular gasoline by the tagging materials therein.

BACKGROUND OF THE INVENTION

Although the prior art discloses hydrocarbon tagging materials having molecular weights of up to 1,200, that art teaches away from using much higher molecular weight materials as tagging materials.

U.S. Pat. No. 4,141,692 teaches using chlorinated compounds as markers. These dyes have a molecular weight of less than 250.

U.S. Pat. No. 4,209,302 teaches using invisible colored dyes. These dyes have a molecular weight of less than 800.

U.S. Pat. No. 4,278,444 teaches using fluorescent dyes as markers. These dyes have a molecular weight of less than 800.

U.S. Pat. No. 4,735,631 teaches substituted anthraquinone tagging compound, which would have a molecular weight of less than 700.

U.S. Pat. No. 4,764,474 teaches using a substituted anthraquinone tagging compound, which would have a molecular weight of less than 700.

U.S. Pat. No. 4,918,020 teaches a method for analyzing marker dyes by using a solid-phase extraction technique with formation of a colored complex in the extraction column.

U.S. Pat. No. 5,234,475 teaches using one or more fullerene additives as tracers in a fuel. It teaches using up to $C_{84}$ fullerenes, which would have a molecular weight of less than 1100.

European Application 0 509 818 A1 teaches silent markers as tracers in petroleum, such as 2,6-bis(1,1-dimethylethyl)-4-[(4-nitrophenyl)azo-phenol]. The disclosed markers all have molecular weights of less than 900.

SUMMARY OF THE INVENTION

The present invention provides a tagged gasoline and a process for identifying hydrocarbon compositions from one another.

In that process, at least one of the hydrocarbon compositions has added to it at least one tagging material which is unique to that composition. Each tagging material has a number average molecular weight of at least 15,000. A sample of the composition is vaporized to form a liquid residue, and the liquid residue is analyzed for the presence of the tagging material to thereby identify the particular hydrocarbon composition. Preferably, each tagging material is present in amounts less than 1.0 ppm of the hydrocarbon composition.

The tagged gasoline contains a detectable amount of at least one tagging material therein serving as identification means for the gasoline. Each tagging material has a number average molecular weight of at least 15,000, and is present in the gasoline in an amount of less than 1.0 ppm of the gasoline. Preferably, the tagging materials have a weight average to number average molecular weight ratio of less than 1.5.

Each unique tagging material must be soluble in the composition to be tagged, must not vaporize or thermally degrade at temperatures below about 120° C., must not contribute to degradation of hydrocarbon filterability: and must not contribute to engine harm.

BRIEF DESCRIPTION OF THE DRAWINGS

In order to assist the understanding of this invention, reference will now be made to the appended drawings. The drawings are exemplary only, and should not be construed as limiting the invention.

DETAILED DESCRIPTION OF THE INVENTION

Figure 1:
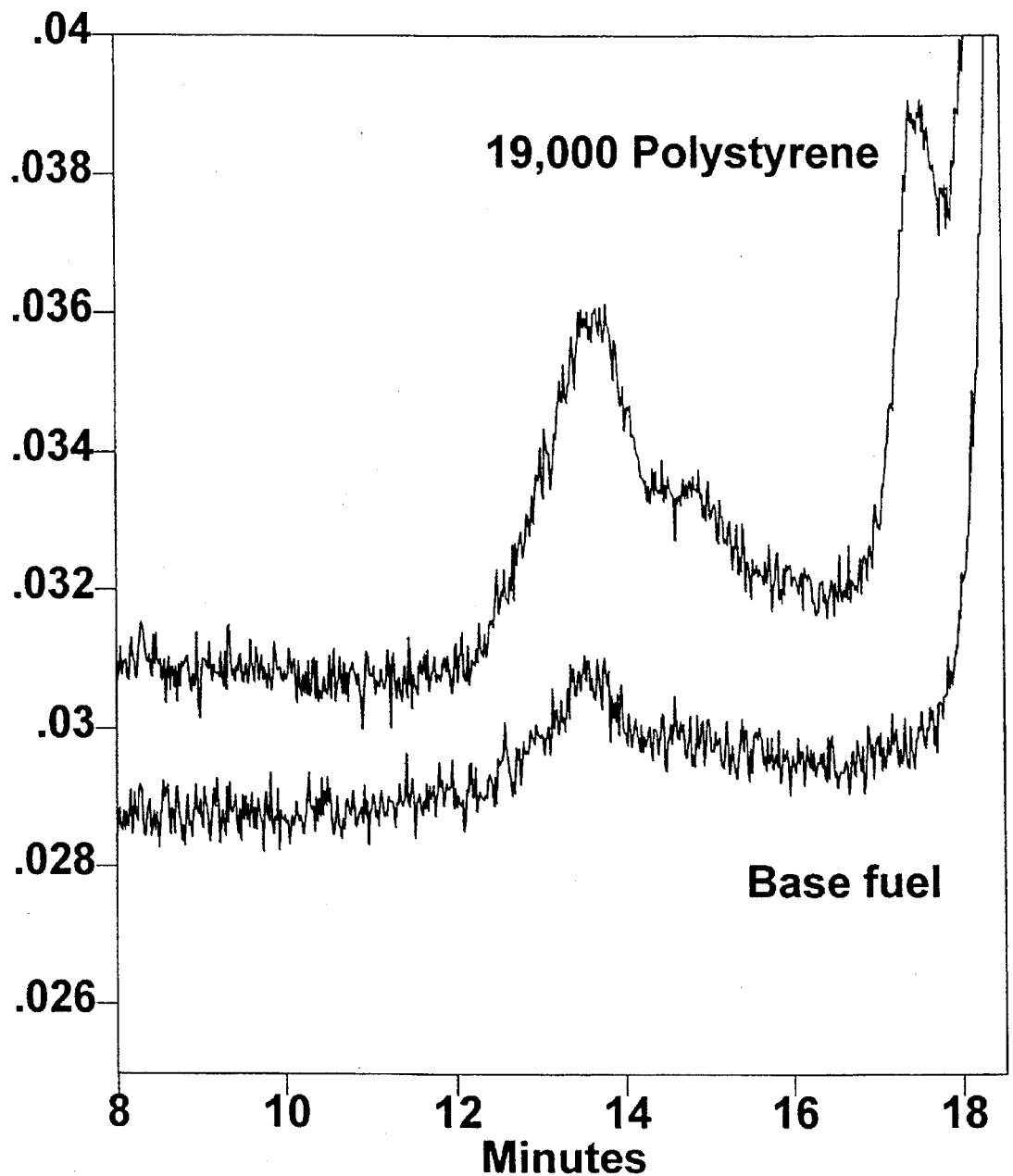
FIG. 1 shows the molecular weight distribution of a fuel concentrate (Example 1) derived from a base gasoline without any tagging material, and the molecular weight distribution of a fuel concentrate (Example 2) derived from the gasoline of Example 1 to which polystyrene having a molecular weight of 19,000 has been added to a concentration of 0.05 ppm.

In its broadest aspect, the present invention involves a hydrocarbon composition containing a detectable amount of at least one tagging material therein serving as identification means for the hydrocarbon composition. Each tagging material used has a number average molecular weight of at least 15,000 and is present in the hydrocarbon composition in an amount of less than 1.0 ppm of the hydrocarbon composition.

THE HYDROCARBON COMPOSITION

The hydrocarbon composition can be any volatile hydrocarbon composition, but this invention is especially useful for tagging gasoline.

THE TAGGING MATERIAL

The hydrocarbon composition contains a detectable amount of at least one tagging material therein that serves as identification means for the hydrocarbon composition.

We have discovered that tagging materials having a number average molecular weight of at least 15,000 are detectable in a volatile hydrocarbon composition at a concentration of less than 1.0 ppm of the hydrocarbon composition if the composition is vaporized to form a liquid residue and the molecular weight distribution of the entire residue is determined. The tagging material appears as a separate peak on the molecular weight distribution.

It is important that the concentration of the tagging material be less than 1.0 ppm in the hydrocarbon composition in order to insure that the presence in the hydrocarbon composition is for tagging purposes. There are a variety of patents, such as U.S. Pat. Nos. 3,682,187 and 3,687,148 that teach the use of high molecular weight block copolymers as drag reducers at concentrations of more than 1 ppm. The presence of a high molecular weight material at a concentration below that effective for drag reduction insures that the material is present as a tagging material and not a drag reducer. U.S. Pat. Nos. 3,682,187 and 3,687,148 are hereby incorporated by reference for all purposes.

More than one tagging material can be used in a hydrocarbon composition. If more than one tagging material is used, then each must be detectable in the hydrocarbon composition. For each tagging material to be detectable, the molecular weight distributions of the tagging materials should not significantly overlap and each tagging material must have a concentration of less than 1.0 ppm.

In addition, each unique tagging material must be soluble in the composition to be tagged, must not vaporize or thermally degrade at temperatures below about 120° C., must not contribute to degradation of hydrocarbon filterability: and must not contribute to engine harm.

Preferably, the tagging material has a weight average to number average molecular weight ratio of less than 1.5, so that its molecular weight distribution can be readily distinguished from that of the hydrocarbon composition that is to be tagged. This narrow molecular weight distribution is especially important where more than one tagging material is used, and in cases of fuels contaminated with high molecular weight material.

As the tagging material may be included as part of an additive package, solubility and chemical and physical stability at much higher concentrations is also desirable.

THE PROCESS

The present invention uses a size exclusion chromatography technique, coupled with evaporative light scattering, to identify trace amounts of high molecular weight materials that act as tracers.

The process identifies hydrocarbon compositions from one another by adding to at least one of the hydrocarbon compositions at least one tagging material which is unique to that composition. Each tagging material has a number average molecular weight of at least 15,000 and is present in the hydrocarbon composition in an amount less than 1.0 ppm of the hydrocarbon composition. A sample of the composition is vaporized to form a liquid residue and the liquid residue is analyzed for the presence of the tagging material in the residue to thereby identify the particular hydrocarbon composition.

By using a material with a number average molecular weight (Mn) of greater than 15,000, and by prevaporizing the fuel, one can use a size exclusion chromatography technique, coupled with evaporative light scattering, to resolve tracer peaks at levels of 0.05 ppm, or lower, even in the presence of normal contaminants. One can use combinations of different high molecular weight materials, each with narrow molecular weight distributions, to identify individual additive components.

EXAMPLES

The invention will be further illustrated by the following examples, which set forth particularly advantageous method embodiments. While the Examples are provided to illustrate the present invention, they are not intended to limit it.

EXAMPLE 1

A 332 gram sample of a regular unleaded gasoline was weighed into a 1-liter flask and attached to a rotary evaporator. The system was purged with nitrogen and vacuum was applied. Under these conditions light ends from the gasoline evaporated and were collected in cold traps. When condensation of light ends in the cold traps was nearly complete, the nitrogen purge was discontinued. The pressure inside the system was 100 mm Hg.

The evaporation flask was then slowly heated under vacuum to a bath temperature of 122° C. At this final temperature, the pressure inside the system was 5 mm Hg. Vacuum was discontinued, the flask was removed from heat, and the material was cooled under nitrogen to near ambient temperature, then the cold traps were emptied. The flask was removed, and the fuel concentrate inside was transferred into a 100-ml flask. A rotary evaporator trap was attached to the flask and the entire apparatus was remounted to the evaporation system. The system was again purged with nitrogen, and then vacuum and heat were applied to the flask until the bath temperature was brought back up to 122° C. After several ml of condensate were obtained in the rotary evaporator trap, the system was again purged and cooled, and the 100-ml flask was weighed, to obtain a final weight of 3.44 g of fuel concentrate.

EXAMPLE 2

A stock solution was prepared by dissolving polystyrene with a nominal number average molecular weight of 19,000 g/mole (available from Tosoh Corp., Japan) in a 100° F. flash point aromatic solvent (Exxon 100 aromatic solvent) to a concentration of 282 ppm. 0.0527 g of this stock solution was added to 300. g of the gasoline of example 1, to result in a final fuel concentration of 0.05 ppm polystyrene. All 300 .g of the gasoline were then vaporized in the fashion of example 1. The final weight of fuel concentrate obtained was 1.82 g.

EXAMPLE 3

A stock solution was prepared by dissolving polystyrene with a nominal number average molecular weight of 4,000,000 g/mole (available from Polymer Laboratories Ltd., UK) in a 100° F. flash point aromatic solvent (Exxon 100 aromatic solvent) to a concentration of 237 ppm. 0.0675 g of this stock solution was added to 305 g of the gasoline of example 1, to result in a final fuel concentration of 0.05 ppm polystyrene. All 305 g of the gasoline were then vaporized in the fashion of Example 1. The final weight of fuel concentrate obtained was 2.44 g.

All three solutions were then chromatographed on a Waters™ HPLC system using an ACS Model 750/14 Evaporative Light Scattering Detector. Critical conditions for the analysis are shown below.

| | |
|---|---|
| Injection Volume | 100 microliters |
| Flow Rate | 1.0 mL/min. |
| Mobile Phase | Toluene |
| Columns | Polymer Laboratories Inc. PLGel ™ 10 micron particle size, $10^4$ angstrom pore size, 7.5 × 300 mm and Phenomenex Phenogel5 ™, $10^5$ angstrom pore size, 7.8 × 300 mm |
| Pump | Waters ™ Model 510 |
| Injector | Waters ™ Model 712 WISP |
| Detector | ACS Model 750/14 Evaporative Light Scattering Detector |
| Detector Evaporator Set | 095 |
| Detector Attenuation Range | ×1 |
| Detector Time Constant | 1 sec |

| | -continued |
|---|---|
| Detector Photomultiplier Sensitivity | ×6 |
| Detector Nitrogen Pressure | 13 psig |
| Run Time | 25 minutes |

The chromatograms of the fuel concentrates prepared in Examples 1 and 2 are shown in FIG. 1. The top chromatogram is that of the solution of Example 2, and the bottom is that of Example 1. The two chromatograms have been offset by a constant additive factor to facilitate comparison. The retention time of the peak at about 17.5 minutes in the chromatogram of the concentrate Example 2 matches that of the peak in a chromatogram taken of the 19,000 g/mole stock solution mentioned in Example 2. This peak, although on the shoulder of the peak resulting from the remainder of the fuel concentrate, is still distinct from the fuel and has very good sensitivity. The peak is of sufficient size that it could be detected at even lower starting concentrations than 0.05 ppm.

The peaks at about 13.5 minutes are surprising, and are believed to be due to contamination from sample containers. It is believed that use of appropriate materials and cleaning procedures will nearly eliminate the peak; however, it is possible that in application to other fuels such contamination will be present. The ability to use appropriate molecular weight materials will be valuable in such cases. Use of tagging materials with a weight average to number average molecular weight ratio of less than 1.5 would be preferable in such cases.

Figure 2:
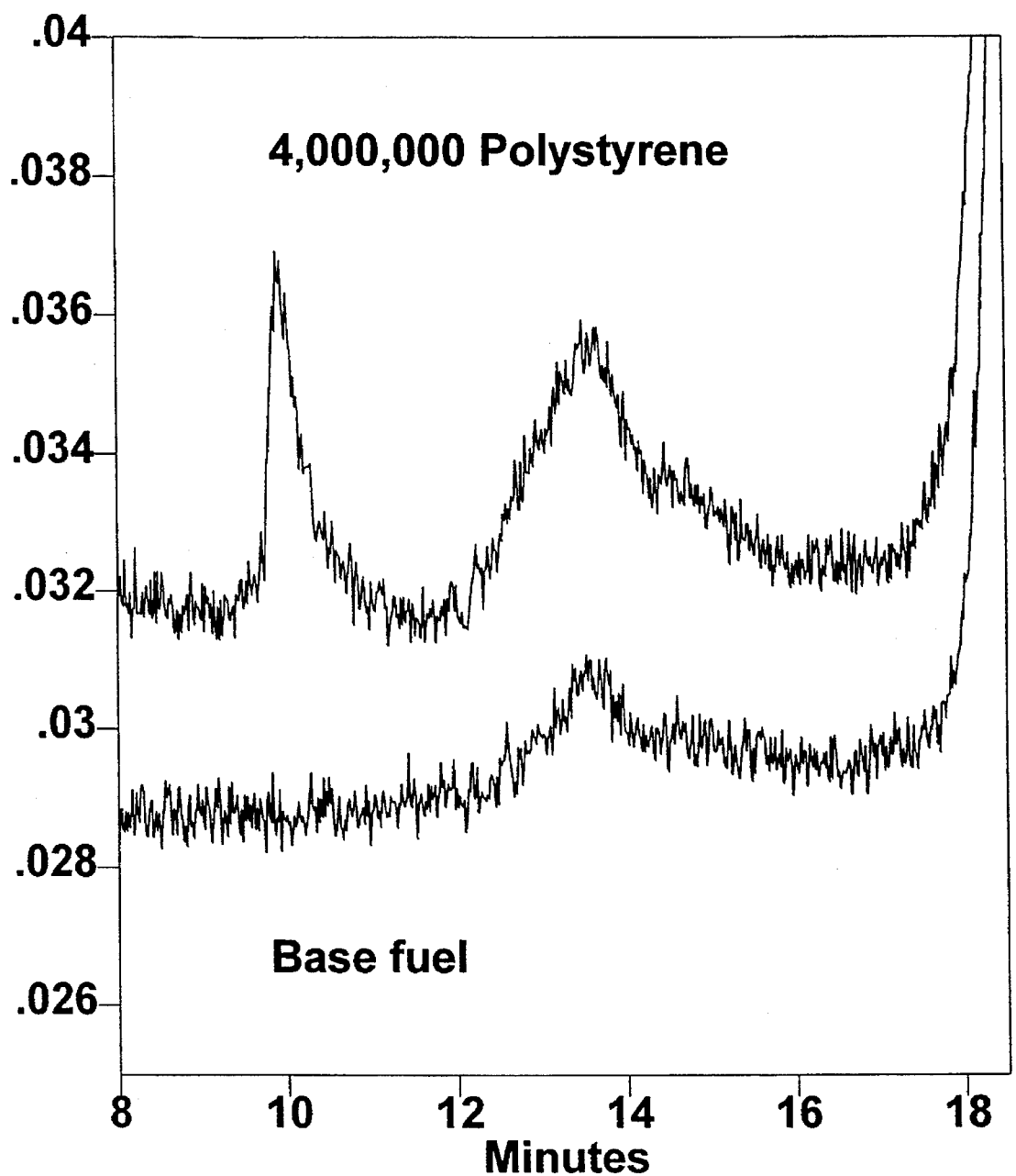
FIG. 2 shows the molecular weight distribution of a fuel concentrate (Example 1) derived from a base gasoline without any tagging material, and the molecular weight distribution of a fuel concentrate (Example 3) derived from the gasoline of Example 1 to which polystyrene having a molecular weight of 4,000,000 has been added to a concentration of 0.05 ppm.

The chromatograms of the fuel concentrates prepared in Examples 1 and 3 are shown in FIG. 2. The top chromatogram is that of the concentrate of Example 3, and the bottom is that of Example 1. The two chromatograms have been offset by a constant additive factor to facilitate comparison. The retention time of the peak at about 10 minutes in the chromatogram of the concentrate Example 3 matches that of the peak in a chromatogram taken of the 4,000,000 g/mole stock solution mentioned in Example 3. This peak is baseline resolved from the peaks due to fuel and to the presumed contamination. The peak is of sufficient size that it could be detected at even lower starting concentrations than 0.05 ppm.

EXAMPLE 4

Simpler methods of evaporation of the marked gasoline may also be used. 52.42 g of the gasoline mentioned in Example 1 was weighed into a clean, dry 150-ml Pyrex beaker. The beaker was set on a hot plate with a surface temperature of 220°–255° F., and blown with nitrogen until nearly dry. The residue was transferred into a vial using toluene to rinse the beaker. The vial was heated on the hot plate under nitrogen to blow off the toluene. The final weight of the residue was 0.6341 g. Similar residues were prepared using this method on the marked gasolines mentioned in Examples 2 and 3. The residues were then chromatographed using the conditions mentioned previously. Chromatograms similar to those of FIGS. 1 and 2 were obtained.

While the present invention has been described with reference to specific embodiments, this application is intended to cover those various changes and substitutions that may be made by those skilled in the art without departing from the spirit and scope of the appended claims.

What is claimed is:

1. A gasoline containing a detectable amount of at least one tagging material therein serving as identification means for the gasoline, wherein the amount of each tagging material present in the gasoline is less than 1.0 ppm of the gasoline, wherein each tagging material has the following properties:

(a) a number average molecular weight of at least 15,000;
    (b) soluble in the composition to be tagged;
    (c) does not vaporize or thermally degrade at temperatures below about 120° C.;
    (d) does not contribute to degradation of hydrocarbon filterability: and
    (e) does not contribute to engine harm.

2. A gasoline according to claim 1 wherein the tagging material has a weight average to number average molecular weight ratio of less than 1.5.

3. A process for identifying hydrocarbon compositions from one another, said process comprising:

(a) adding to at least one of the hydrocarbon compositions at least one tagging material which is unique to that composition, wherein each tagging material has the following properties:
        (1) a number average molecular weight of at least 15,000;
        (2) soluble in the composition to be tagged;
        (3) does not vaporize or thermally degrade at temperatures below about 120° C.;
        (4) does not contribute to degradation of hydrocarbon filterability: and
        (5) does not contribute to engine harm;
    (b) vaporizing a sample of the composition to form a liquid residue; and
    (c) analyzing the liquid residue for the presence of the tagging material in the residue to thereby identify the particular hydrocarbon composition.

4. A process according to claim 3 wherein the amount of each tagging material present in the hydrocarbon composition is less than 1.0 ppm of the hydrocarbon composition.

* * * * *